United States Patent
Hildenbrand

Patent Number: 6,126,900
Date of Patent: *Oct. 3, 2000

[54] GRAPHITE NONWOVENS AS FUNCTIONAL LAYERS IN DIAGNOSTIC TEST KITS

[75] Inventor: Karlheinz Hildenbrand, Krefeld, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/798,386

[22] Filed: Feb. 7, 1997

[30] Foreign Application Priority Data

Feb. 15, 1996 [DE] Germany ............ 196 05 582

[51] Int. Cl.⁷ ............................................. G01N 33/49
[52] U.S. Cl. ................. 422/56; 436/63; 436/169
[58] Field of Search ................. 422/56, 58, 61, 422/73; 436/169, 808, 63

[56] References Cited

U.S. PATENT DOCUMENTS

| | | |
|---|---|---|
| 4,012,325 | 3/1977 | Columbus . |
| 4,477,575 | 10/1984 | Vogel et al. ............ 436/170 |
| 4,753,776 | 6/1988 | Hillman et al. . |
| 5,055,195 | 10/1991 | Trasch et al. . |
| 5,266,179 | 11/1993 | Nankai et al. . |
| 5,290,420 | 3/1994 | Matson . |
| 5,370,993 | 12/1994 | Tarnowski et al. .......... 435/7.21 |

FOREIGN PATENT DOCUMENTS

| | | |
|---|---|---|
| 269240 | 6/1988 | European Pat. Off. . |
| 2559242 | 7/1976 | Germany . |
| WO 94/27140 | 11/1994 | WIPO . |

OTHER PUBLICATIONS

Chemie in unserer Zeit 15, (1981), 21 ff.

*Primary Examiner*—Lyle A. Alexander
*Attorney, Agent, or Firm*—Norris McLaughlin & Marcus

[57] ABSTRACT

The present invention relates to the use of graphite nonwovens and graphite woven fabrics for removing cellular constituents from blood and corresponding test agents for analysis of blood constituents.

4 Claims, 1 Drawing Sheet

GRAPHITE NONWOVENS AS FUNCTIONAL LAYERS IN DIAGNOSTIC TEST KITS

BACKGROUND OF THE INVENTION

1. Field of the Invention

The present invention relates to the use of graphite nonwovens and graphite woven fabrics for removing cellular constituents from blood and corresponding test agents for analysis of blood constituents.

2. Description of Related Art

The separation of serum or plasma from whole blood is of overriding importance in clinical chemistry. In particular, many diagnostic detection reactions of blood components proceed without impairment only after the red blood corpuscles have been separated off. This particularly applies to colour reactions which are evaluated either by reflectometry or visually, or also electrochemically.

The most common form for separating off erythrocytes is centrifugation. However, this presents problems with small blood samples in particular, so that a whole series of aids are known for this, as described, for example, in German Auslegeschrift 25 59 242.

The use of special erythrocyte retention substrates in the field of whole blood analysis with the aid of test strips, such as blood sugar monitoring under home user conditions, is of particular importance.

As prior art, multi-layer test systems comprising a reagent layer and an erythrocyte separation zone comprising at least one or more glass fibre layers, which may be different, have proved themselves here (U.S. Pat. No. 4,477,575).

The whole blood is applied to the glass fibre layer, the erythrocytes being adsorbed into this layer as a consequence of agglutination, while plasma and serum diffuse into the reagent layer, where the detection reaction can proceed without interference by erythrocytes.

As described in EP 0 133 895, the glass fibre layer can comprise auxiliary reagents, such as certain polar dyestuffs, which have the effect of coagulation or agglutination of the erythrocytes.

According to German Offenlegungsschrift 30 29 579, the glass fibres can be loosely stacked and processed in the form of papers, nonwovens or felts, columns packed with glass fibres also being claimed. According to U.S. Pat. No 4,477,575, the glass fibres used can have a diameter in the range from 0.2 to 5.0 $\mu$m and be in the density range from 0.1 to 0.5 g/cm$^2$.

A disadvantage of the diagnostic test systems with erythrocyte retention substrates of glass fibre nonwovens is their relatively high requirement of whole blood volumes, which are about 10 $\mu$l for the known Reflotron® glucose test systems. However, smaller amounts of blood, for example 5 $\mu$l or less, are of great advantage, in particular in respect of obtaining the blood as painlessly as possible.

Another important disadvantage of the glass fibre nonwovens is their low mechanical strength, which is even significantly below the values such as are known, for example, for thin blotting papers.

Mechanical working, for example cutting or impregnation using conventional machines which require certain tear strengths, is made exceptionally difficult as a result.

WO 94/27140 describes erythrocyte retention layers of porous membrane matrices which comprise, for example, dextrans, polylysines, polybrenes or protamines as agglutinating agents. However, compared with the abovementioned glass fibre systems, these membrane layers are more complicated to produce and are not so variable in respect of layer thickness, absorption volume and flow or transportation properties, it being impossible, in particular, to realize horizontal, chromatography-like transportation functions, such as are required for realization of certain test strip formats (for example FIG. 4 in U.S. Pat. No. 4,477,575).

As in the case of the abovementioned white glass fibre layers, after application of blood an intense red discoloration of the retention layers occurs. Because of this red background coloration, undesirable interference problems may occur in reflectometric evaluation of the reagent layers on top.

SUMMARY OF THE INVENTION

It has now been found, surprisingly, that nonwovens of graphite fibres can meet the requirements imposed on the erythrocyte separation function in an outstanding manner without the abovementioned disadvantages occurring.

BRIEF DESCRIPTION OF THE DRAWINGS

The invention will now be described in more detail with reference to the drawings, wherein.

DESCRIPTION OF THE PREFERRED EMBODIMENTS

Figure 1:
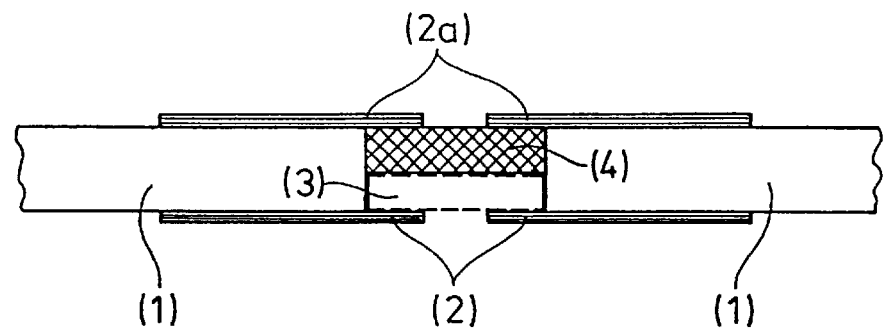
FIG. 1 is a diagram showing in cross-section the various layers of a multi-layer sandwich test system according to the present invention.

Such graphite nonwovens are produced by the company SGL Carbon Group, the type Sigrafil SPC 7011 having proved to be particularly suitable for the erythrocyte separation layers according to the invention.

These are black nonwovens of high tear strength comprising graphite fibres with an average fibre diameter of 7 $\mu$m, a weight per unit area of 30 g/m$^2$, a thickness of 0.5 mm and a binder system of crosslinked polyvinyl alcohol, the content of which is about 20 to 24% by weight.

Woven fabrics which can also be produced from graphite fibres and are marketed under the name Sigratex® are also suitable for preparation of the erythrocyte retention layers according to the invention.

As a consequence of this very hydrophilic polymeric binder, the Sigrafil® graphite nonwovens moreover are distinguished by an excellent wettability. Similarly to glass fibre nonwovens, a very rapid transportation of liquid is to be observed both in the horizontal and in the vertical direction. It has been possible to achieve similarly good results with the Sigrafil type SPC 7016, which differs from the type 7011 mentioned above by a higher layer thickness (0.8 mm).

Other suitable nonwovens which are possible for separating off erythrocytes are the Sigratherm® papers, which are produced from carbon staple fibres and are likewise marketed by SGL Carbon Group.

The high tear strengths of about 160 N/5 cm of these graphite nonwovens are to be mentioned in particular, so that there are no processing problems with conventional processing machines which require certain tear strengths.

The separation of the erythrocytes with the aid of the graphite nonwovens described, the average fibre diameter of which is 7 μm, is to be described as surprising in as much as, according to U.S. Pat. No. 4,777,575, glass fibre nonwovens with fibre diameters in this range should no longer be suitable for removal of erythrocytes.

Thus, it can be seen in Table 2 from U.S. Pat. No. 4,477,575 that glass fibre nonwovens having fibre diameters of more than 2 μm are no longer suitable for plasma or serum separation.

Two further important advantages of the graphite nonwoven erythrocyte retention substance according to the invention result from its black colour. After application of the blood, for example onto a two layer test system of the retention layer and reagent membrane, the red erythrocytes retained in the graphite nonwoven can scarcely still be detected visually, which is to be evaluated as an aesthetic advantage. This advantage also manifests itself in the reflectometric evaluation of the colour reaction in the reagent membrane, because in contrast to the conventional systems (red-coloured, erythrocyte-containing glass fibre layers as a background), no adverse reflectometric interferences can result.

The graphite nonwovens according to the invention impregnated with known agglutinating agents, such as lectins, can be used as one- or multi-layer systems. In the case of multi-layer retention substrates, all or also only individual graphite nonwoven layers can be impregnated with one or various agglutinating agents. Multi-layer retention substances can also comprise other porous layers, such as polyvinyl alcohol nonwovens or mono- or multifilament woven fabrics, as elemental components, in addition to graphite nonwovens.

It is essential only that the main content of the agglutinated erythrocytes is retained in a graphite nonwoven layer, and that preferably the top layer (application of blood) and the layer closest to the reagent membrane are made of graphite nonwoven.

Another typical property of the graphite nonwovens is their electrical conductivity, which is in the region of a few ohms typical of carbon fibres.

As a result of the combination of electrical conductivity with the outstanding property of horizontal transportation of liquid, layers with bifunctional functions can be built up in respect of electrochemical sensor systems. As shown in more detail in Example 2, in an amperometric test format a graphite nonwoven layer can simultaneously perform the function of liquid-drawing microcapillaries (a mode of application popular in biosensors (European Patent Application 0 471 986)), and simultaneously function as a reference electrode.

EXAMPLES

Example 1

Visual Blood Sugar Test a) Erythrocyte Retention Layer

A graphite nonwoven (SPC 7011 from SGL) was impregnated with the following solution and then dried with hot air:

0.04 g of lectin (from potatoes, SERVA, potato lectin) was dissolved in 1.5 ml of the following Cremophor EL surfactant solution:

97.60 g of water 0.85 g of Cremophor EL (Sigma, C 5135)

2.20 g of HEPES buffer 0.5 M (Sigma, H 7006); pH 7.5 b) Reagent Layer

Preparation of the Membrane Matrix (Analogously to Deutsche Auslegeschrift 4 308 150)

From 20.0 g of Dralon L (polyacrylonitrile, Bayer AG)

180.0 g of Ultrason E (polyether sulphone, BASF)

20.0 g of Aerosil 200 (highly disperse silicic acid, Degussa)

90.0 g of Pluriol P 900 (polypropylene glycol, BASF)

413.4 g of N-methyl-2-pyrrolidone NMP, Riedel deHaën)

a casting solution was prepared with a high-speed stirrer and, after degassing, was coated onto a polyester nonwoven (FO 2402, from Freudenberg) with the aid of a doctor blade and coagulated in water (40° C.).

A porous, carrier-supported membrane (average pore size about 5 to 8 μm) was obtained and, after drying, was used for the following impregnation:

Impregnation of the Polymer Blend Membrane

Impregnating solution 1:

15.0 mg of peroxidase (618 U/mg)

50.0 mg of 3-methyl-2-benzothiazolinone hydrazone hydrochloride 7.5 ml of methanol 7.5 ml of potassium phosphate buffer 0.1 mol/l pH 7.0

Impregnating solution 2:

100.0 mg of 3-dimethylaminobenzoic acid 7.5 ml of methanol 7.5 ml of potassium phosphate buffer 0.1 mol/l pH 7.0

Impregnating solution 3:

77.25 mg of glucose oxidase (151 U/mg)

15.0 ml of potassium phosphate buffer 0.1 mol/l pH 7.0

After drying with hot air, the reagent membrane was obtained. A multi-layer test system for blood sugar detection was built up in accordance with the diagram which follows.

Sandwich Construction: Colour Reaction Read from the Underneath

The construction is shown in FIG. 1.

1: Test strip holder, perforated

2: Transparent, perforated covering films

3: Reagent membrane

4: Impregnated graphite nonwoven

The blood was applied via the opening at 2a), and on the opposite side a blue colour reaction which was unimpaired by erythrocytes and correlated with the glucose concentration of the whole blood was to be observed after a few seconds.

The blood constituents had penetrated completely into the graphite nonwoven, so that after the reaction, because of the black colour of the nonwoven, no "red residues" at all were to be detected, which is to be evaluated as an aesthetic advantage compared with the prior art. It was possible to limit the amount of blood to be applied to 5 μl for layer diameters (reagent membrane, graphite nonwoven) of 5 mm.

Capillary Flow System: Observation of the Colour Reaction from the Top

Figure 2:
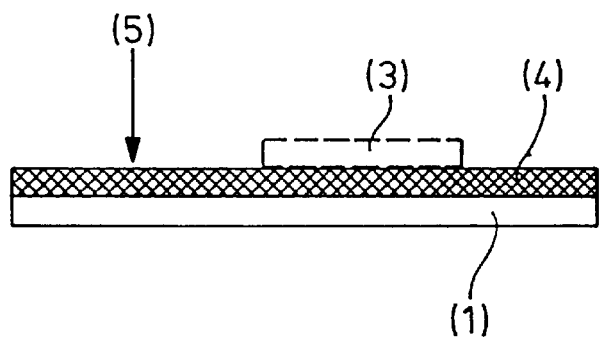
FIG. 2 is a diagram showing in cross-section the various layers of a multi-layer capillary flow test system according to the present invention.

The construction is shown in FIG. 2.

1: Test strip holder

2: Impregnated graphite nonwoven

3: Reagent membrane

The whole blood was applied at 5, and a few seconds later a colour reaction unimpaired by red erythrocytes was to be observed on the surface of the reagent membrane 3.

As the glucose concentrations of the test solutions increased, increasing blue colour intensities were observed.

Example 2
Visual Cholesterol Test

The erythrocyte retention layer of the reagent membrane was prepared and the test strip constructed analogously to Example 1.

Impregnating Recipe for the Reagent Membrane

Impregnating solution 1:
- 15.0 mg of peroxidase (618 U/mg)
- 50.0 mg of 3-methyl-2-benzothiazolinone hydrazone hydrochloride
- 7.5 ml of methanol
- 7.5 ml of potassium phosphate buffer 0.1 mol/l pH 7.0

Impregnating solution 2:
- 100.0 mg of 3-dimethylaminobenzoic acid
- 7.5 ml of methanol
- 7.5 ml of potassium phosphate buffer 0.1 mol/l pH 7.0

Impregnating solution 3:
- 16.0 mg of cholesterol oxidase (24.3 U/mg)
- 9.0 mg of cholesterol esterase (118 U/mg)
- 500 µl of potassium phosphate buffer 0.1 mol/l pH 7.0

The reagent membrane was dried at 45° C. in a circulating air drying cabinet.

During testing with whole blood (samples of different cholesterol contents), blue colour reactions, the colour intensities of which correlated with the particular cholesterol concentrations, were observed.

Example 3
Amperometric Test Kit

Figure 3:
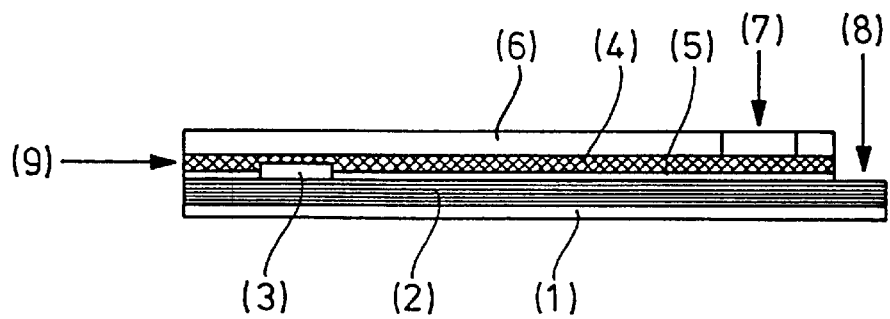
FIG. 3 is a diagram showing in cross-section the various layers of a multi-layer amperometric test system according to the present invention.

The construction is shown in FIG. 3.
1: Carrier film (base film)
2: Conductive layer (for example graphite, gold or palladium)
3: Porous dielectric layer (membrane or nonwoven)
4: Graphite nonwoven
5: Double-sided adhesive tape
6: Top film
7: Contact with the reference electrode
8: Contact with the working electrode
9: Application of the sample liquid With the aid of a potentiostat, the voltage of which was set at 400 mV and which was contacted in accordance with the above diagram, chronamperometric measurements (for the principles cf., for example, Chem. in unserer Zeit 15 (1981) 21 et seq.) were carried out. The test solutions used, which were applied via the graphite nonwoven front edge (9) with the aid of a pipette, were ferri/ferrocyanate test solutions, the following series of sample liquids being analysed:

1. $K_3Fe(CN)_6$ (potassium hexacyanoferrate), 200 mmol in water (stock solution)
2. 2 mmol of $K_4Fe(CN)_6$ in 198 mmol of stock solution
3. 4 mmol of $K_4Fe(CN)_6$ in 196 mmol of stock solution
4. 6 mmol of $K_4Fe(CN)_6$ in 194 mmol of stock solution
5. 8 mmol of $K_4Fe(CN)_6$ in 192 mmol of stock solution
6. 10 mmol of $K_4Fe(CN)_6$ in 190 mmol of stock solution In the chronamperometric evaluation, current curves which decrease with $1/t^{1/2}$ were found in the µA range in accordance with the Cotrell equation, increasing current yields being achieved with increasing $K_4Fe(CN)_6$ concentrations.

I claim:

1. A device for conducting a diagnostic test reaction, said device comprising multiple layers joined one on top of another, wherein one of said layers comprises a graphite nonwoven layer comprising a binder system of crosslinked polyvinyl alcohol, the content of said binder system being about 20 to 24% by weight of said graphite nonwoven layer and another of said layers comprises a reagent for reacting with a sample.

2. The device according to claim 1, wherein said graphite nonwoven layer further comprises an agglutination agent or a red blood corpuscle retention agent.

3. A method of conducting a diagnostic test reaction, said method comprising applying an amount of a sample to be tested to said graphite nonwoven layer of the device according to claim 1 and determining the extent of the reaction in said reagent layer between said sample and said reagent.

4. The method according to claim 3, wherein the sample to be tested is blood, said reagent in said reagent layer reacts with a non-cellular constituent of blood, and said graphite nonwoven layer further comprises an agglutination agent or a red blood corpuscle retention agent.

* * * * *